United States Patent [19]
Reagen et al.

[11] Patent Number: 6,051,436
[45] Date of Patent: Apr. 18, 2000

[54] METHOD FOR THE DETECTION OF NITRO-CONTAINING COMPOSITIONS USING ULTRAVIOLET PHOTOLYSIS

[75] Inventors: William K. Reagen, Stillwater, Minn.; Gregory D. Lancaster, Idaho Falls, Id.; Judy K. Partin, Idaho Falls, Id.; Glenn A. Moore, Idaho Falls, Id.

[73] Assignee: Lockheed Idaho Technologies Company, Idaho Falls, Id.

[21] Appl. No.: 08/285,584

[22] Filed: Aug. 3, 1994

[51] Int. Cl.⁷ ................................................. G01N 33/00
[52] U.S. Cl. .......................... 436/106; 436/107; 436/110; 436/116; 436/172; 436/181; 422/52
[58] Field of Search ............................... 422/52; 436/106, 436/107, 110, 153, 172, 181, 116–118

[56] References Cited

U.S. PATENT DOCUMENTS

| | | | |
|---|---|---|---|
| 2,863,060 | 12/1958 | Willis | 250/346 |
| 3,410,663 | 11/1968 | Reilly et al. | 436/110 X |
| 3,578,410 | 5/1971 | Van Luik, Jr. | 436/36 |
| 3,906,226 | 9/1975 | Okabe et al. | 250/304 |
| 3,973,910 | 8/1976 | Fine | 436/107 |
| 4,102,201 | 7/1978 | Trine et al. | 73/863.21 |
| 4,199,682 | 4/1980 | Spector et al. | 250/339.05 |
| 4,233,030 | 11/1980 | Twitchett et al. | 422/70 X |
| 4,252,537 | 2/1981 | Cattran et al. | 436/111 |
| 4,350,660 | 9/1982 | Robinson et al. | 422/90 |
| 4,381,922 | 5/1983 | Frey et al. | 422/98 |
| 4,485,308 | 11/1984 | Rabatin | 250/461.1 |
| 4,788,039 | 11/1988 | Glattstein | 422/61 |
| 4,851,687 | 7/1989 | Ettinger et al. | 376/159 X |
| 4,882,121 | 11/1989 | Grenier | 376/159 |
| 4,987,767 | 1/1991 | Corrigan et al. | 73/23.36 |
| 5,006,299 | 4/1991 | Gozani et al. | 376/159 |
| 5,080,856 | 1/1992 | Grenier et al. | 376/159 |
| 5,094,815 | 3/1992 | Canbay et al. | 422/52 |
| 5,114,662 | 5/1992 | Gozani et al. | 376/159 |
| 5,124,554 | 6/1992 | Fowler et al. | 376/159 X |
| 5,300,441 | 4/1994 | Fujinari et al. | 436/110 |
| 5,364,795 | 11/1994 | Sausa et al. | 436/106 |

OTHER PUBLICATIONS

Yu. A. Zakharov et al, *Chem. Abstr.* 1970, 72, 138306 X.
J.M. Cooley et al. *Can. J. Chem.* 1980, 58, 627–630.
B.O. Budevska et al. *J. Chromatogr.* 1986, 351, 501–505.
W.R. LaCourse et al. *Anal. Chem.* 1987, 59, 1366–1372.
G.L. Petriconi et al. *Chem. Abstr.* 1970, 72, 105837t.
D.E.G. Shuker et al. *Anal. Chem.* 1983, 55, 2152–2155.
B.A. Keller et al. *J. Phys. Chem.* 1987, 91, 1114–1120.
J.J. Conboy et al. *Analyst* 1989, 114, 155–159.
M.D. Pace *J. Phys. Chem.* 1991, 95, 5858–5864.
J.S. Stamler et al. *Proc. Natl. Acad. Sci. USA* 1992, 89, 7674–7677.
G.W. Lemire et al. *Anal. Chem.* 1993, 65, 529–533.
A. Marshall et al. *Analyst* 1994, 119, 1719–1724.
MacCraith, B.D. et al., "Fibre Optic Sensor for Nitrates in Water", *Society of Photo–optical Instrumentation Engineers — Chemical and Medical Sensors,* 1510:195–203 (1991).

(List continued on next page.)

*Primary Examiner*—Arlen Soderquist
*Attorney, Agent, or Firm*—Klaas Law O'Meara & Malkin

[57] ABSTRACT

A method for detecting nitro-containing compositions (e.g. nitrate/nitrite materials) in water samples and on solid substrates. In a water sample, ultraviolet light is applied to the sample so that dissolved nitro compositions therein will photolytically dissociate into gaseous nitrogen oxides ($NO_2$ $_{(g)}$ and/or $NO_{(g)}$). A carrier gas is then introduced into the sample to generate a gaseous stream which includes the carrier gas combined with any gaseous nitrogen oxides. The carrier gas is thereafter directed into a detector. To detect nitro-compositions on solid substrates, ultraviolet light is applied thereto. A detector is then used to detect any gaseous nitrogen oxides which are photolytically generated during ultraviolet illumination. An optional carrier gas may be applied to the substrate during illumination to produce a gaseous stream which includes the carrier gas and any gaseous nitrogen oxides. The gaseous stream is then supplied to the detector.

2 Claims, 3 Drawing Sheets

OTHER PUBLICATIONS

Wekof, A., "Treatment of Contaminated Water, Air and Soil with UV Flashlamps", *Environmental Progress,* 10(4):241–247 (Nov. 1991).

Fainberg, A., "Explosives Detection for Aviation Security", *Science,* 255:1531–1537 (Mar. 20, 1992).

Bongiovanni, R. et al., "Analysis of Trace Amounts of Six Selected Poly–Nitro Compounds in Soils", *American Industrial Hygiene Association Journal,* 45:222–226 (Apr. 1984).

Burrows, W.D. et al., "Tertiary Treatment of Effluent From Holston AAP Industrial Liquid Waste Treatment Facility v. Degradation of Nitramines in Holston AAP Wastewaters by Ultraviolet Radiation", *Technical Report 8602 — U.S. Army Medical Bioengineering Research and Development Laboratory,* Sep. 1986.

Technical Literature Document on Toximet™ Electrochemical Cell Detectors by Enmet Corporation of Ann Arbor, MI (undated – 2 pages).

Technical Data Sheets on Model 8841 Analyzer for Nitrogen Oxides by Monitor Labs of Englewood, CO (undated – 2 pages).

Technical Data Sheets on Model 8840 Chemiluminescent Nitrogen Oxides Analyzer by Monitor Labs of Englewood, CO (undated – 2 pages).

Technical Data Sheets on Model 8550 Dynamic Calibrator by Monitor Labs of Englewood, CO (undated – 2 pages).

Vogt, W., "Soil Sensors Boost Management Precision", *Solutions,* pp. 26–27 (Mar./Apr. 1992).

Catalog entitled "UV–VIS–IR Monochromators & Illumination Systems" by Spectral Energy Corp. of Westwood, NJ (undated).

A.W. Adamson et al., *Concepts of Inorganic Photochemistry,* John Wiley & Sons, New York, 1975 (pp. 185–189).

Instructions for Sensor Evaluation Kit re Odyssey 2001, Transducer Research, Inc., Naperville, IL (2001/AN 5.0 Rev. 1) — Mar. 20, 1992 (pp. 1–8).

American Public Health Association, American Water Works Association, and Water Pollution Control Federation, *Standards for the Examination of Water and Wastewater,* American Public Health Association, Washington, D.C. pp. 4–2 to 4–6 and 4–131 to 4–143 (1989).

Treinin, A., "The Photochemistry of Oxyanions", *Israel Journal of Chemistry,* 8:103–113 (1970).

Treinin, A. et al., "Absorption Spectra and Reaction Kinetics of $NO_2$, $N_2O_3$, and $N_2O_4$ in Aqueous Solution", *Journal of the American Chemical Society,* 92(20):5821–5828 (Oct. 7, 1970).

METHOD FOR THE DETECTION OF NITRO-CONTAINING COMPOSITIONS USING ULTRAVIOLET PHOTOLYSIS

CONTRACTUAL ORIGIN OF THE INVENTION

The United States Government has rights in this invention pursuant to Contract No. DE-AC07-76ID01570 between the U.S. Department of Energy and EG&G Idaho, Inc.

BACKGROUND OF THE INVENTION

The present invention generally relates to the analytical detection of nitro-containing compositions including nitrate and nitrite materials, and more particularly to the detection of such materials in water samples and on solid substrates using ultraviolet photolysis.

Current developments in chemical technology have created a corresponding need for rapid and accurate chemical detection methods. This need exists in a wide variety of technical fields. For example, excess nitrate and nitrite materials in ground and surface water can cause numerous problems. High levels of dissolved nitrate and/or nitrite compositions in ground and surface water are generally a consequence of large-scale inorganic fertilizer application. Improper or inadequate sewage treatment may also result in the contamination of water and soil materials with human/animal waste matter. The biological decomposition of such matter releases nitrate materials into the water and surrounding soil, thereby causing contamination problems. As a general rule, increased levels of nitrate and nitrite materials in ground and surface water occur through the leaching of dissolved inorganic nitrates and decomposition of organic nitrogen-containing compounds to form highly mobile nitrate ions ($NO_3^-$) and nitrite ions ($NO_2^-$). In aqueous environments, nitrate contamination dominates over nitrite contamination since nitrite ions are easily oxidized to form nitrate ions.

In both surface and ground water, it is important to accurately monitor dissolved nitrate and/or nitrite materials on a qualitative and quantitative basis. In the United States, the National Academy of Sciences (NAS) Committee on Water Quality Criteria recommends that the level of nitrate nitrogen in public water supplies not exceed 10.0 mg of nitrate nitrogen/liter of water and 1.0 mg of nitrite nitrogen/liter of water. These parameters are likewise endorsed by the United States Environmental Protection Agency (EPA) Office of Drinking Water. Nitrate and nitrite ion levels in drinking water which exceed the foregoing amounts can produce various health problems. For example, one problem of substantial concern involves an illness commonly known as "blue baby syndrome" experienced by infants which are bottle fed using water containing large quantities of nitrate ions. Because infants normally have a low level of digestive tract acidity, their digestive systems are capable of supporting the growth of bacteria which reduce ingested nitrates to nitrites. These nitrites thereafter enter the circulatory systems of the infants and ultimately cause a substantial reduction in blood oxygen-carrying capacity. Oxygen-deficient blood exhibits a characteristic blue color, thereby supporting the term "blue baby syndrome". The inadequate transport of oxygen in this manner can result in numerous health problems, including but not limited to arrested physical and mental development. Furthermore, studies have indicated that increased consumption of nitrate materials (including nitrate ions in water) can cause stomach cancer, as well as other illnesses.

Many attempts have been made in the past to quantitatively and qualitatively analyze nitrate and nitrite ion levels in water. For example, one commonly-used method involves ion chromatography in accordance with American Public Health Association (APHA) Method Number 4110. Ion chromatography involves the use of sophisticated chromatographic systems, and is capable of sequentially analyzing water samples for nitrate and nitrite levels. The applicable range of nitrate analysis using ion chromatography is about 0.03–3.4 mg of nitrate nitrogen/liter of water.

Another commonly-used nitrate analysis method involves cadmium reduction in accordance with APHA Method Number 4500-$NO_3^-$E. This method involves the reduction of nitrate ions to nitrite ions in the presence of cadmium. The resulting nitrite ions are then diazotized with sulfanilamide and subsequently coupled with N-(1-naphthyl)-ethylenediamine dihydrochloride to form a highly colored dye solution. The dye solution is thereafter calorimetrically analyzed, with the ultimate nitrate concentration being determined using a calibration curve. The detection range associated with this method is about 0.01–1.0 mg of nitrate nitrogen/liter of water.

An additional technique involves the use of an ultraviolet spectrophotometer system in accordance with APHA Method Number 4500-$NO_3^-$B. This method specifically uses an ultraviolet spectrophotometer in which ultraviolet light is applied to a liquid sample, followed by measurement of the ultraviolet absorbance characteristics of the sample. Such measurements are made without any dissociation or chemical alteration of the nitrate ions. In particular, this method measures nitrate concentrations using ultraviolet absorbance at about 220 nm, with an applicable detection range of about 0.02–11 mg of nitrate nitrogen/liter of water. However, ultraviolet spectrophotometry is not recommended for use with sample materials having substantial amounts of organic compositions therein. Such compositions may interfere with the spectrophotometer system. Other materials which may cause similar interference problems include but are not limited to various commercial surfactants and $Cr^{+6}$ ions. It should likewise be noted that a variation of the foregoing method exists which involves the use of a fiber optic-based ultraviolet spectrophotometer system for continuous water monitoring as discussed in MacCraith, B. D., et al., "Fiber Optic Sensor for Nitrates in Water", *Society of Photooptical Instrumentation Engineers—Chemical and Medical Sensors,* 1510:195–203 (1991).

Notwithstanding the foregoing analytical methods and systems, a need exists for a method suitable for detecting nitrate/nitrite materials and other nitro-containing compositions which is rapid, efficient, and avoids the use of multi-step processes involving potentially dangerous chemical reagents (including but not limited to cadmium compounds and the like). Furthermore, a need exists for a detection method involving the foregoing materials which substantially avoids interference problems associated with organic materials, metal ions, and the like. The present invention satisfies this goal by providing a highly effective analytical process for detecting nitrate and/or nitrite ions in water (as well as dissolved non-ionic nitro-containing compounds) which is characterized by an absence of expensive and potentially toxic chemical reagents, as well as a minimal degree of complexity.

Efficient detection methods are likewise needed in order to detect nitro-containing compositions (e.g. nitrate and/or nitrite materials) on solid substrates. For example, the detection of nitrate and nitrite compounds ranging from fertilizers to explosive compositions is of current interest. The qualitative detection of nitro-containing compositions having explosive capabilities is especially important in connection with packaging materials, luggage, and related products. In recent years, a demand has developed for technology involving the detection of explosive compositions in airports and other public areas vulnerable to terrorist activities. Considerable interest exists in the rapid detection of explosives in trace amounts on luggage, shipping crates, and packages wrapped with paper, cloth, and the like. Also, it is desirable in many cases to detect such materials in soil and on human skin. Most modern explosives have physical characteristics which cause the adhesion thereof to solid objects. As a result, trace amounts of explosives are often found on the exterior surfaces of articles containing the explosives and on individuals handling the explosives. Detection of such trace amounts can be used to identify explosive articles and terrorist activities. Also, the detection of explosive materials in this manner may be useful in environmental decontamination/remediation processes at military installations and the like.

Many types of nitro-containing compositions having explosive capabilities are currently in use. For example, the following exemplary explosive materials are of particular concern:

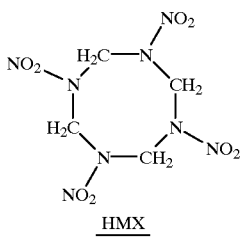

HMX (1,2,3,5,7-Tetranitro-1,3,5,7-tetraazacyclooctane)

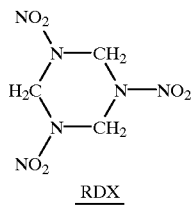

RDX (1,3,5-Trinitro-1,3,5-triazacyclohexane)

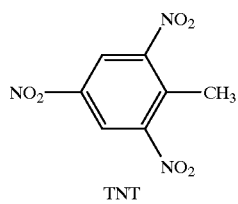

TNT (2,4,6-Trinitrotoluene)

NH₄NO₃ ammonium nitrate

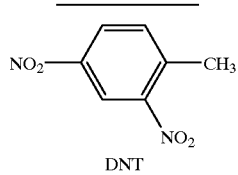

DNT (2,4-Dinitrotoluene)

-continued

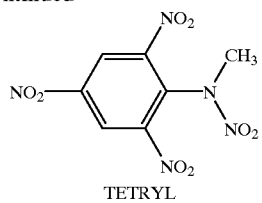

TETRYL (2,4,6-Trinitrophenylmethylnitramine)

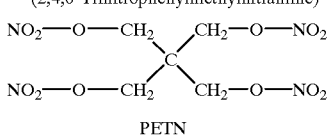

PETN (Pentaerythritol tetranitrate)

Other explosive materials of interest include nitroglycerin, watergels, nitrocellulose, and potassium nitrate. It should be noted that the present invention shall not be limited to the detection of any particular nitrate, nitrite, and nitro-containing compositions, and shall likewise not be restricted to detection of the foregoing explosives which are provided for example purposes. Regarding the detection of explosives and other nitro-containing compositions, numerous methods have been investigated. For example, thermal neutron analysis has been used in which thermal neutrons react with nitrogen in the test materials (e.g. nitro-type explosives) to generate gamma rays as described in U.S. Pat. No. 4,851,687. X-ray detection methods have also been used in connection with nitro-containing compositions. In particular, dual energy systems based on established theories involving Compton scattering may be used for detection purposes as generally discussed in Fainberg, A., "Explosives for Aviation Security", *Science,* 255:1531–1537 (Mar. 20, 1992).

Regarding the detection of nitrate/nitrite materials and other nitro-containing compositions, a number of additional techniques have been employed including (1) electron capture analysis; (2) gas chromatography; (3) ion mobility spectrometry; and (4) ultraviolet spectrometry. Further techniques involving the detection of nitro-containing compositions are discussed in Bongiovanni, R., et al., "Analysis of Trace Amounts of Six Selected Poly-Nitro Compounds in Soils", *Am. Ind. Hyg. Assoc. J.,* 45(4):222–226 (1984), as well as in U.S. Pat. Nos. 5,124,554; 5,114,662; 5,080,856; 5,006,299; 4,987,767; 4,882,121; 4,851,687; 4,788,039; 4,252,537; and 3,410,663.

Notwithstanding the foregoing analytical systems, a need remains for an effective method designed to detect the presence of nitro-containing compositions (including explosive materials) on solid substrates which is rapid, efficient, sensitive, and avoids the use of elaborate processing techniques. Furthermore, a need exists for such a method which is effective, yet portable and suitable for use in public places. The present invention satisfies this need by providing a highly efficient analytical process for detecting trace amounts of nitro-containing compositions (e.g. explosives and various nitrate/nitrite materials) on solid materials including but not limited to soil, packaging components, shipping crates, and containers.

SUMMARY OF THE INVENTION

It is an object of the present invention which to provide a rapid and effective method for detecting nitro-containing compositions.

It is another object of the invention to provide a method for detecting nitro-containing compositions which is readily applicable to the detection of nitrate ions, nitrite ions, and dissolved non-ionic nitro-containing compounds (e.g. dissolved explosive compounds such as TNT) in water samples.

It is another object of the invention to provide a method for detecting nitro-containing compositions which is readily applicable to the detection of such materials in trace amounts on solid substrates.

It is a further object of the invention to provide a method for detecting nitro-containing compositions which is readily implemented in a portable, easily transported system.

It is a further object of the invention to provide a method for detecting nitro-containing compositions which is characterized by the absence of elaborate processing equipment and potentially toxic chemical reagents.

It is an even further object of the invention to provide a method for detecting nitro-containing compositions which enables the sampling and analysis of such materials in a safe manner without requiring technical personnel to come in direct physical contact therewith.

It is an even further object of the invention to provide a method for detecting nitro-containing compositions which uses ultraviolet photolysis to generate gaseous nitrogen oxides therefrom, with such gaseous nitrogen oxides being subsequently detected in a safe and effective manner.

In accordance with the foregoing objects, the present invention involves a unique and highly efficient method for detecting nitro-containing compositions (e.g. nitrate and nitrite compositions) in a variety of different environments. For the purposes of the present invention, use of the terms "nitrate composition" and "nitrite composition" shall encompass the detection of both nitrate and nitrite ions ($NO_3^-$ and $NO_2^-$) in solution, as well as solid compositions containing at least one nitrate group (—$NO_3$) and/or at least one nitrite (—$NO_2$) group. The broader term "nitro-containing composition" as used herein shall encompass the detection of nitrate and/or nitrate compositions (as defined above) in liquid or solid form, as well as solid or liquid materials having the general structure $(R_xN_yO_z)_n$ wherein R=one or more organic or inorganic moieties and "x", "y", "z", and "n" are each of the value 1 or more. The foregoing organic moieties may include but not be limited to straight or branched chain groups, cyclic or acyclic groups, aromatic groups, and/or cycloaliphatic groups. Exemplary inorganic moieties may consist of metals, metal complexes, metal cations, halides, sulfates, and/or oxides. The nitrogen and oxygen bonds within any of the foregoing structures applicable for detection using the present invention may include single or multiple bonds, and likewise may be bridged, pi, or sigma bonded. The foregoing nitro-containing compositions as defined herein may involve neutral species, charged species, or mixtures of both. Specific compositions having the basic $(R_xN_yO_z)_n$ structure which may be detected as described herein include nitro, nitrate, nitrite, nitroamine, nitramine, nitroalkane, and/or nitroso compounds. Thus, while the present invention shall be primarily described herein in connection with nitrate and/or nitrite compositions, it shall likewise be applicable regarding many other nitro-containing compositions as described above. Finally, the terms "solid material", "solid composition", and "solid substrate" as used herein shall not be limited to any particular solid materials. Exemplary solid compositions for which nitro-compound (e.g. nitrate and/or nitrite) testing is desired include but are not limited to soil samples, commercial packaging materials, containers manufactured from various materials, human skin, and the like.

In a first embodiment of the invention, the qualitative or quantitative analytical detection of nitrate ions, nitrite ions, and/or dissolved non-ionic nitro-containing compounds within a water sample is accomplished with a high degree of accuracy. All of these materials shall be collectively referred to hereinafter as "dissolved nitro-containing compositions". A water sample is first obtained for which testing is desired. Thereafter, an ultraviolet light source is provided which is capable of generating ultraviolet light having a continuous spectral wavelength output (e.g. spectral distribution) of at least about 220–550 nm at a power output level of about 0.5–500 W (about 5–50W=optimum). These wavelength and power output ranges are sufficient to photochemically dissociate dissolved nitro-containing compositions (as defined above) in the water. However, ultraviolet light sources having an even broader spectral output range may also be used. For the purposes of this invention, the term "nitrogen-containing ions" shall be encompassed within the general term "dissolved nitro-containing compositions" as noted above, and shall specifically consist of nitrate ions ($NO_3^-$), nitrite ions ($NO_2^-$), and mixtures thereof. As far as nitrogen-containing ions are concerned, photochemical dissociation in the foregoing manner generates gaseous nitrogen oxides (e.g. $NO_{(g)}$ and/or $NO_{2(g)}$) in accordance with the following reactions:

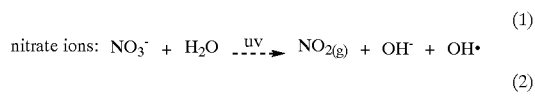

Reaction (1) is not entirely understood and represents the best current understanding of the photolytic process as discussed in Trenin, A., "The Photochemistry of Oxyanions", *Israel Journal of Chemistry*, 8:103–113 (1970); Trenin, A., et al., "Absorption Spectra and Reaction Kinetics of $NO_2$, $N_2O_3$, and $N_2O_4$ in Aqueous Solution", *Journal of the Am. Chem. Soc.*, 92(20):5821–5828 (1970); and Adamson, A. W., et al., *Concepts of Inorganic Photochemistry*, (pp. 185–188), John Wiley and Sons, New York (1975). Reaction (1) involves both hydroxyl ion ($OH^-$) and hydroxyl radical ($OH^\bullet$) formation in a highly complex manner.

Of primary interest in connection with water samples is the detection of nitrogen-containing ions therein as described above. However, as previously noted, dissolved non-ionic nitro-containing compounds may also be detected. The term "dissolved non-ionic nitro-containing compound" as used herein generally involves a composition which is solvated to a very high dilution within the solvent of concern (e.g. water). The phrase "high dilution" normally constitutes a situation in which (1) there is a very large relative distance between the solvated molecular units; and (2) the solvent (water) molecules are intimately associated with the solvated molecules through, for example, polar and dielectric interactions. Exemplary dissolved non-ionic nitro-containing compounds will include various dissolved explosives such as TNT (2,4,6-trinitrotoluene), RDX (1,3,5-trinitro-1,3,5-triazacyclohexane), HMX (1,2,3,5,7-tetranitro-1,3,5,7-tetraazacyclooctane), and PETN (pentaerythritol tetranitrate). As far as these materials are concerned, photochemical dissociation using ultraviolet light will produce gaseous nitrogen oxides (e.g. $NO_{2(g)}$ alone or in combination with $NO_{(g)}$) in a manner comparable to that described above in connection with the listed reactions. Unless otherwise stated herein, all of the information provided below regarding the detection of nitrogen-containing ions shall therefore be equally applicable to dissolved non-ionic nitro-containing compounds which shall be deemed equivalent to nitrogen-containing ions for the purposes of this invention. Accordingly, both of these materials shall be encompassed under the term "dissolved nitro-containing compositions" as described above.

In a preferred embodiment, the ultraviolet light source will consist of an ultraviolet flash lamp, although other ultraviolet sources known in the art may be used including but not limited to mercury vapor lamps and comparable devices. Likewise, the numerical parameters set forth herein are provided for example purposes, and the present invention shall not be exclusively limited to the use of such parameters. Variations within the numerical ranges provided below will be based on differences in sample materials being analyzed and the reaction conditions associated therewith. The selection of proper parameters for any given situation may be undertaken in accordance with preliminary pilot studies involving the materials to be analyzed and the equipment being used.

The selected water sample is illuminated with ultraviolet light from the ultraviolet light source over a time period of about 15–300 seconds (about 30–120 seconds=optimum) in a preferred embodiment to convert dissolved nitro-containing compositions (e.g. nitrogen-containing ions) in the water sample into gaseous nitrogen oxides (e.g. $NO_{2(g)}$ and/or $NO_{(g)}$). For most applications of the invention, it is preferred that the ultraviolet light source be maintained at a distance not exceeding about 10 cm (about 2–10 cm=optimum) from the water sample during illumination with ultraviolet light. In addition, illumination can occur above the surface of the water sample (e.g. outside of the water sample) or within the water sample using a conventional optical fiber bundle or cable connected to the light source in which the terminal end of the cable is immersed in the water sample. Optical fiber materials and the technology associated therewith are well known in the art.

As described above, application of ultraviolet light to the water sample generates gaseous nitrogen oxides, with the phrase "gaseous nitrogen oxides" being defined herein to encompass $NO_{(g)}$ and/or $NO_{2(g)}$. Most of the photolytically-generated gaseous nitrogen oxides remain within the water sample. To effectively remove any gaseous nitrogen oxides from the water sample for detection purposes, at least one carrier gas is passed through the water sample (e.g. at a preferred flow rate of about 25–1000 cc/min [about 100–300 cc/min.=optimum]) in order to sparge the water sample and remove gaseous nitrogen oxides therefrom. In an optimum embodiment, a carrier gas is selected from the group consisting of air, $N_2$, $O_2$, Ar, and other inert gases. If air is desired as the carrier gas, it is preferable that nitrogen oxide-free air be used. However, normal (untreated) air may be used in association with a preliminarily-derived calibration curve which takes into account ambient levels of gaseous nitrogen oxides in the air.

Passing of the carrier gas through the water sample generates a gaseous stream which passes out of the water sample. The gaseous stream comprises the carrier gas in combination with any photolytically-generated gaseous nitrogen oxides. To accurately detect and/or measure the amount of gaseous nitrogen oxides in the stream, detector means is provided. Many different types of detecting systems known in the art may be used for this purpose, including but not limited to commercially-available chemiluminescence nitrogen oxide detectors or electrochemical detector cells as further discussed below. While these detecting systems are preferred, other systems may also be used including ion mobility spectrometers and the like. The detector means is supplied with the gaseous stream as it leaves the water sample. This is accomplished by placing the detector means (or various sampling components which are attached to and part of the detector means) directly adjacent the water sample so that the gaseous stream comes in contact with and enters the detector means as the stream exits the sample. In an alternative embodiment, the gaseous stream is supplied to the detector means using suction means for generating a negative pressure (e.g. a vacuum). The suction means is in fluid communication with the detector means (e.g. directly connected to or part of the detector means) so that the gaseous stream is drawn directly into the detector means. The suction means may involve many different structural components, including a vacuum pump system. In a preferred embodiment, the detector means will comprise a tubular conduit member having a first end operatively connected to the detector means and a second end configured in the form of a funnel-shaped collecting member. A vacuum pump functioning as the suction means will be positioned in-line within the conduit member. To operate the suction means, the funnel-shaped collecting member is positioned directly adjacent the water sample to collect the gaseous stream as it leaves the sample. The pump (suction means) is then activated in order to draw the gaseous stream through the conduit member and into the detector means. Thereafter, the detector means is activated to provide a qualitative and/or quantitative analysis of gaseous nitrogen oxides within the gaseous stream. The presence of nitrogen oxides in the gaseous stream over and above any baseline nitrogen oxides in the carrier gas provides qualitative evidence that the water sample contained dissolved nitro-containing compositions therein (e.g. nitrate and/or nitrite ions). The quantity of nitrogen oxides in the gaseous stream may be used to indicate the amount of dissolved nitro-containing compositions in the water sample.

The foregoing method provides highly efficient results while using a minimal amount of equipment. Likewise, the method is characterized by an absence of potentially harmful chemical reagents and avoids direct physical contact by human personnel with the water sample being tested. Both of these goals are accomplished through the ultraviolet photolytic generation and subsequent detection of gaseous nitrogen oxides. This aspect of the invention is a substantial departure from prior detection systems used in connection with nitro-containing compositions.

In a second embodiment of the invention, a method for qualitatively or quantitatively detecting nitro-containing compositions on solid materials is provided. These compositions can involve many different materials ranging from plastic explosives to fertilizers. The foregoing compositions may be detected on a wide variety of solid substrates ranging from soil to packaging materials and human skin. Accordingly, this embodiment of the invention shall not be limited regarding the type of nitro-containing compositions (e.g. nitrate/nitrite compositions) being detected, as well as the solid materials to be tested. In the regard, the term "nitro-containing compositions" shall encompass the same materials listed above. Furthermore, this embodiment of the present invention shall not be limited to any specific numerical parameters which are provided for example purposes. Variations within the listed numerical ranges will be based on differences in sample materials being analyzed, as well as reaction conditions associated therewith. The selection of proper parameters for any given situation may be undertaken in accordance with preliminary pilot studies involving the materials to be analyzed and the equipment being used.

In accordance with this embodiment, a sample of solid material is initially obtained. The solid material may involve may different compositions including but not limited to wood, metal, paper, cloth, plastic, glass, human skin, and the like. Thereafter, an ultraviolet light source is provided which is capable of generating ultraviolet light having a continuous spectral wavelength output (e.g. spectral distribution) of at least about 220–550 nm at a power output level of about 0.5–500 W (about 5–50W=optimum). These wavelength and power output ranges are sufficient to photolytically dissociate nitro-containing compositions (e.g. nitrate and/or nitrite compositions) which are present on the solid material. However, ultraviolet light sources having an even broader spectral output range may also be used. Ultraviolet light is then applied directly to the sample of solid material so that the solid material is illuminated therewith. As a result, gaseous nitrogen oxides (e.g. $NO_{(g)}$ and/or $NO_{2(g)}$) are generated (evolved) from any nitro-containing compositions on the solid material. In a preferred embodiment, the ultraviolet light source will consist of an ultraviolet flash lamp, although other light sources known in the art may be used including but not limited to standard mercury vapor lamps. It is also preferred that the sample of solid material be illuminated with ultraviolet light from the light source for a time period of about 15–300 seconds (about 30–120 seconds=optimum), with the light source being maintained at a distance of about 1–20 cm (about 2–10 cm=optimum) from the solid material.

To quantitatively and/or qualitatively detect any gaseous nitrogen oxides (e.g. $NO_{(g)}$ and/or $NO_{2(g)}$) evolved from the solid material during ultraviolet illumination, detector means is provided. Many different detector systems may be employed, including but not limited to commercially available chemiluminescence nitrogen oxide detectors or electrochemical detector cells. While these specific systems are preferred, other systems known in the art for gaseous nitrogen oxide detection may also be used, including ion mobility spectrometers.

To detect any gaseous nitrogen oxides generated during ultraviolet illumination, the detector means (or sampling components attached to and part of the detector means) is positioned directly adjacent the sample. The detector means is then activated to determine if any gaseous nitrogen oxides were generated (evolved) during the illumination process. The presence of gaseous nitrogen oxides provides a positive indication that the sample of solid material had at least one nitro-containing composition (e.g. nitrate and/or nitrite compound) thereon. Depending on the specific detector means being used, further information may be obtained including quantitative data regarding the amount of generated gaseous nitrogen oxides. This quantitative information may be correlated with standardized data curves to provide accurate information regarding the amount of nitro-containing compositions (e.g. nitrate/nitrite compositions) on the solid material.

In a modification of the foregoing process, suction means for generating a negative pressure (e.g. a vacuum) is optionally provided to facilitate complete delivery of any gaseous nitrogen oxides to the detector means. The suction means is in fluid communication with the detector means (e.g. directly connected to or part of the detector means) so that any evolved gaseous nitrogen oxides are drawn directly into the detector means. The suction means may involve many different structural components, including a vacuum pump system. In a preferred embodiment, the detector means will comprise a tubular conduit member having a first end operatively connected to the detector means and a second end configured in the form of a funnel-shaped collecting member. A vacuum pump functioning as the suction means will be positioned in-line within the conduit member. To operate the suction means, the funnel-shaped collecting member is positioned directly adjacent the sample of solid material during ultraviolet illumination. The pump is then activated in order to draw any gaseous nitrogen oxides through the conduit member and into the detector means. Thereafter, the detector means is activated to provide a qualitative and/or quantitative analysis of gaseous nitrogen oxides.

In a further optional modification of the foregoing process, a stream of at least one carrier gas may be passed over the sample of solid material during ultraviolet illumination. As a result, a gaseous stream is generated which includes the carrier gas in combination with any gaseous nitrogen oxides generated during illumination. This technique facilitates complete delivery of any gaseous nitrogen oxides to the detector means. Likewise, it isolates the gaseous nitrogen oxides from the surrounding environment during delivery to the detector means. The gaseous stream is then supplied to the detector means so that it may be analyzed. In a preferred embodiment, the carrier gas is selected from the group consisting of air, $N_2$, $O_2$, Ar, and other inert gases. If air is desired as the carrier gas, it is preferable that nitrogen oxide-free air be used. Nitrogen oxide-free air may be obtained in the same manner described above regarding the analysis of water samples. However, normal (untreated) air may also be used in association with a preliminarily-derived calibration curve which takes into account ambient levels of gaseous nitrogen oxides in the untreated air. In a preferred embodiment, the carrier gas will be passed over the sample material at a flow rate of about 25–1000 cc/min. (about 100–300 cc/min.=optimum).

Supplying of the gaseous stream to the detector means may be accomplished by placing the detector means (or sampling components attached to and part of the detector means) in direct proximity with the stream as it leaves the solid substrate. Alternatively, suction means of the same type described above may be used to ensure complete delivery of the gaseous stream to the detector means. If suction means were used, the funnel-shaped collecting member would be placed directly in the path of the gaseous stream. The pump would then be activated in order to draw the gaseous stream through the conduit member and into the detector means.

In a still further embodiment of the invention, the foregoing method may be used to determine the presence of a specific explosive material (or other nitro-containing composition) by using ultraviolet light having a specific wavelength (or wavelength range) known to dissociate the composition of interest. For example, if the detection a specific explosive is desired, ultraviolet light having a wavelength known to dissociate the explosive is applied to the sample of solid material. Thereafter, the previously-described steps are used (including the use of detector means) to determine if any gaseous nitrogen oxides are generated. Because most ultraviolet light sources will generally produce a broad spectral wavelength output, a selected wavelength control system will be used to obtain ultraviolet light of the desired wavelength characteristics. Exemplary wavelength control systems will include but not be limited to monochromators and bandpass filter units as described in greater detail below. If gaseous nitrogen oxides are present, it can be concluded that the solid material had the explosive composition (or other nitro-containing composition) of interest thereon. It should be noted that this embodiment of the invention shall not be exclusively limited to the detection of explosive materials, and is applicable to other nitrogen-containing compositions (e.g. nitrogen-containing fertilizers and other materials) having known ultraviolet dissociation wavelengths. The foregoing embodiment may also involve the optional use of suction means and/or a carrier gas in the same manner described above. Furthermore, depending on the specific detector means being used, additional information may be obtained including quantitative data regarding the amount of generated gaseous nitrogen oxides. This quantitative information may be correlated with standardized data curves to provide accurate information regarding the amount of designated nitro-containing composition on the solid material. Finally, this variation of the invention involving the use of a wavelength control system to detect specific nitro-containing compositions is also applicable to the detection of such materials in water samples as described in greater detail below.

The foregoing detection method and its various embodiments provides highly efficient results while requiring a minimal amount of equipment. Furthermore, the method may be implemented using a system which is highly portable. Both of these goals are accomplished through the ultraviolet photolytic generation and subsequent detection of gaseous nitrogen oxides. This aspect of the invention is a substantial departure from prior detection systems involving nitro-containing compositions.

The present invention represents a significant advance in the art of nitro-composition detection. These and other objects, features, and advantages of the invention shall be described below in the following Brief Description of the Drawings and Detailed Description of Preferred Embodiments.

DETAILED DESCRIPTION OF PREFERRED EMBODIMENTS

In accordance with the present invention, a highly-efficient method for qualitatively and/or quantitatively detecting the presence of nitro-containing compositions (e.g. nitrate compositions and/or nitrite compositions) is disclosed. As previously indicated, the terms "nitrate composition" and "nitrite composition" shall encompass the detection of both nitrate and nitrite ions ($NO_3^-$ and $NO_2^-$) in solution, as well as solid compositions containing at least one nitrate group ($-NO_3$) and/or at least one nitrite ($-NO_2$) group. The present invention shall not be restricted regarding the type of nitrate/nitrite materials which can be detected. The broader term "nitro-containing composition" as used herein shall encompass the detection of nitrate and/or nitrate compositions (as defined above) in liquid or solid form, as well as solid or liquid materials having the general structure $(R_xN_yO_z)_n$ wherein R=one or more organic or inorganic moieties and "x", "y", "z", and "n" are each of the value 1 or more. The foregoing organic moieties may include but not be limited to straight or branched chain groups, cyclic or acyclic groups, aromatic groups, and/or cycloaliphatic groups. Exemplary inorganic moieties may consist of metals, metal complexes, metal cations, halides, sulfates, and/or oxides. The nitrogen and oxygen bonds within any of the foregoing structures applicable for detection using the present invention may include single or multiple bonds, and likewise may be be bridged, pi, or sigma bonded. The foregoing nitro-containing compositions as defined herein may involve neutral species, charged species, or mixtures of both. Specific compositions having the basic $(R_xN_yO_z)_n$ structure which may be detected as described herein include nitro, nitrate, nitrite, nitroamine, nitramine, nitroalkane, and/or nitroso compounds. Thus, while the present invention shall be primarily described herein in connection with nitrate and/or nitrite compositions, it shall likewise be applicable regarding many other nitro-containing compositions as described above.

A. Detection of Nitro-Containing Compositions in Water Samples

Figure 1:
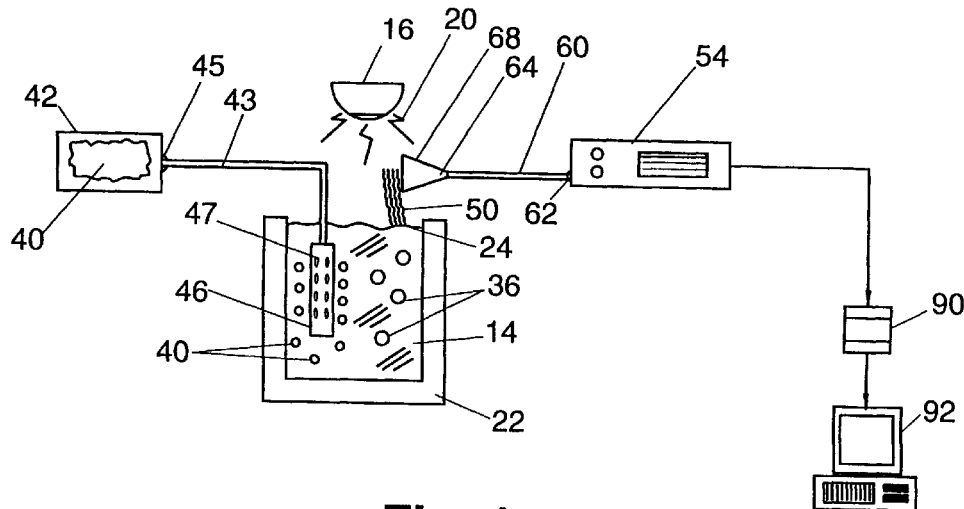
FIG. 1 is a schematic representation of an exemplary process used in connection with a first embodiment of the present invention to detect dissolved nitro-containing compositions (e.g. nitrate and/or nitrite ions) in a water sample.

In a first embodiment of the invention, dissolved nitro-containing compositions are detected in a water sample on a quantitative or qualitative basis using a minimal amount of test equipment. Also, detection is accomplished without the need for technical personnel to come in direct contact with the water sample being tested. With reference to FIG. 1, a schematic illustration of the process steps and equipment used to implement water testing for dissolved nitro-containing compositions is provided. The method associated with FIG. 1 shall not be limited to any specific types of equipment, structural components, or numerical parameters which are described herein for example purposes.

As illustrated in FIG. 1, a water sample 14 is initially provided for testing. The water sample 14 may be derived from a number of different sources, and may involve ground water, water from lakes or streams, agricultural run-off water, water from industrial facilities, and the like. The present invention shall not be limited to any particular source from which the water sample 14 is obtained. In connection with a preferred embodiment of the invention, the water sample 14 will be analyzed for the presence of nitrogen-containing ions therein. For the purposes of this invention, the term "nitrogen-containing ions" shall be encompassed with the general term "nitro-containing compositions" as noted above, and shall specifically consist of nitrate ions ($NO_3^-$), nitrite ions ($NO_2^-$), and mixtures thereof. Of primary interest in connection with the water sample 14 is the detection of nitrogen-containing ions as defined above. However, dissolved non-ionic nitro-containing compounds may also be detected. These materials and examples thereof are described above. Photochemical/photolytic dissociation of such materials as discussed herein will produce gaseous nitrogen oxides (e.g. $NO_{(g)}$ and/or $NO_{2(g)}$) in a manner comparable to that which occurs regarding nitrogen-containing ions. Unless otherwise stated herein, all of the information described below regarding the detection of nitrogen-containing ions shall be equally applicable to dissolved non-ionic nitro-containing compounds as defined above. Accordingly, both of these materials shall be encompassed under the term "dissolved nitro-containing compositions" as previously noted.

To qualitatively and/or quantitatively detect dissolved nitro-containing compositions (e.g. nitrate and/or nitrite ions) in the water sample 14, an ultraviolet light source 16 is provided. The light source 16 may involve many different ultraviolet illumination systems, and the present invention shall not be limited to any particular type of ultraviolet light source 16. The light source 16 should be capable of generating continuous or pulsed ultraviolet light having a continuous spectral wavelength output (e.g. spectral wavelength range distribution) of at least about 220–550 nm at a power output level of about 0.5–500 W (about 5–50 W=optimum). However, ultraviolet light sources having an even broader spectral output range may also be used as long as the foregoing preferred range is encompassed therein. As further described below, these parameters are sufficient to cause the photolytic dissociation of nitrogen-containing ions and other dissolved nitro-containing compounds in the water sample 14 in order to generate gaseous nitrogen oxides (defined herein to encompass $NO_{2(g)}$, $NO_{(g)}$ and mixtures thereof) therefrom. However, the precise parameters to be selected in connection with the light source 16 in any given situation will depend on a variety of factors including the type of light source 16 being used and the environment in which testing takes place. Specific wavelengths and power output levels for any given situation may ultimately be determined in accordance with preliminary pilot studies.

As noted above, the light source 16 (and most ultraviolet light sources) will not generate a single ultraviolet wavelength, but will instead generate ultraviolet light in the form of a continuum encompassing a broad spectral wavelength range which includes the range of interest described above (e.g. at least about 220–550 nm). A preferred system suitable for use as the light source 16 will consist of a battery-operated ultraviolet flash lamp operating at a pulse frequency of about 1–22 Hz. An exemplary commercial flash lamp appropriate for the purposes set forth herein will consist of a 24 V xenon flash lamp system sold by EG&G Electro-Optics, Inc of Salem, Mass. (USA) under the designation "MVS-2602/FX-249UV". Another system which may be used as the light source 16 involves a standard 1000 W mercury vapor lamp capable of producing a continuous light output. However, flash lamp units of the type described above are preferred in view of their low cost, portability, and high efficiency. Various additional ultraviolet light sources which may be used in all embodiments of the present invention are commercially available from Spectral Energy Corp. of Westwood, N.J. (USA).

The application of ultraviolet light 20 from the light source 16 illustrated in FIG. 1 causes photolytic dissociation of any dissolved nitro-containing compositions in the water sample 14 to produce gaseous nitrogen oxides therefrom. As far as nitrate/nitrite ions are concerned, photolytic dissociation thereof using ultraviolet light is generally illustrated in the following reactions:

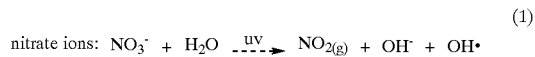

As noted above, reaction (1) is not entirely understood and represents the best current understanding of the photolytic dissociation process.

Reactions (1) and (2) demonstrate how gaseous nitrogen oxides are generated from nitrate/nitrite ions during illumination of the water sample 14 with ultraviolet light 20 from the light source 16. As far as dissolved non-ionic nitro-containing compounds are concerned, photochemical dissociation will produce gaseous nitrogen oxides (e.g. $NO_{2(g)}$ alone or in combination with $NO_{(g)}$) in a manner comparable to that described above in connection with the listed reactions. The exact reaction products and quantities thereof will vary, depending on the type of materials involved. Detailed information regarding reaction products generated during dissociation of dissolved non-ionic nitro-containing compounds may be determined prior to actual testing in connection with preliminary pilot investigations.

In a preferred embodiment for both quantitative and qualitative purposes, the size of water sample 14 will optimally range from about 5–50 ml. The water sample 14 may be placed in any type of vessel 22 which will allow the passage of ultraviolet light therethrough. Preferred materials used to manufacture vessel 22 include glass and/or quartz. An exemplary vessel 22 suitable for the purposes set forth herein will involve a cylindrical sample cell commercially available from International Crystal Labs, Inc. of Garfield, N.J. (USA) (product designation: Type 34–50 mm-Q) which is manufactured from glass with a plurality of quartz windows therein.

In most cases, it is preferred that the ultraviolet light source 16 be maintained at a distance not exceeding about 10 cm (about 2–10 cm=optimum) from the water sample 14 during ultraviolet illumination. Illumination can occur above the surface of the water sample 14 (e.g. outside of the water sample 14 and vessel 22) as shown in FIG. 1, or directly within the water sample 14. If the ultraviolet light 20 is applied outside of the water sample 14, it is preferred that a light pattern be used which covers all of the water sample 14 and vessel 22. As illustrated schematically in FIG. 2, the introduction of ultraviolet light 20 into the water sample 14 below the surface 24 thereof may be accomplished using a conventional optical fiber bundle or cable 26 connected to the light source 16 in which the terminal end 30 of the cable 26 is immersed within the water sample 14. Optical fiber materials and the technology associated therewith are well known in the art. For example, representative optical fiber materials suitable for delivering ultraviolet light 20 to the water sample 14 are commercially available from Fostek, Inc. of Auburn, N.Y. (USA). An exemplary optical fiber bundle suitable for use as the cable 26 will be about 18 in. long, and will consist of a plurality of fused quartz fibers bundled together to create a structure having a diameter of about 0.5 in.

Figure 2:
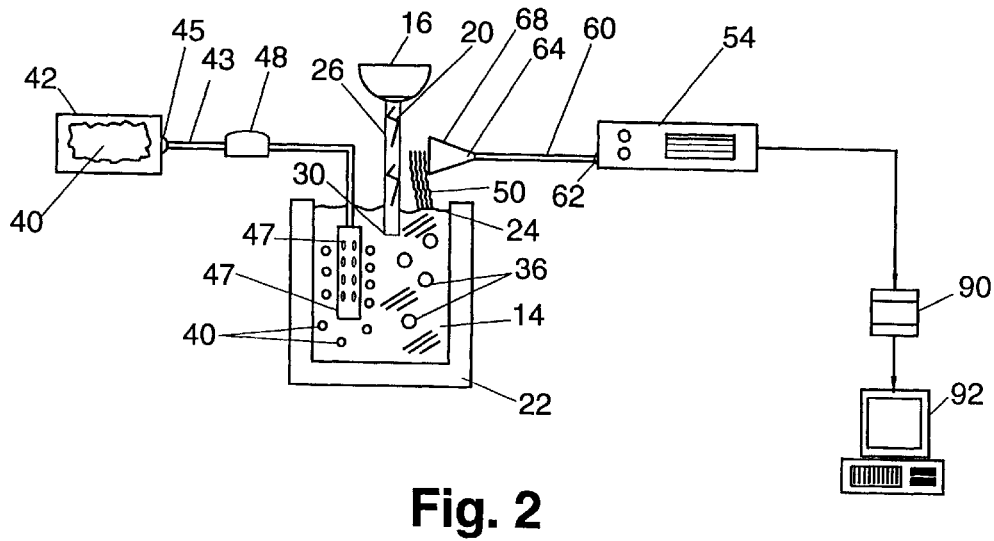
FIG. 2 is a schematic representation of a modification to the process of FIG. 1 which involves the use of an optical fiber system to deliver ultraviolet light into the water sample.

In the embodiments of FIGS. 1–2, it is preferred that the ultraviolet light 20 be applied to or within the water sample 14 for a duration of about 15–300 seconds (about 30–120 seconds=optimum). However, this range and the other numerical parameters set forth herein are provided for example purposes only. Exact reaction conditions and parameters may vary in connection with the equipment being used and the character of the water sample 14.

In accordance with the foregoing procedures, gaseous nitrogen oxides 36 (e.g. $NO_{(g)}$ and/or $NO_{2(g)}$) which are generated from dissolved nitro-containing compositions (e.g. nitrate/nitrite ions) in the water sample 14 primarily remain within the sample 14 (FIG. 1). The gaseous nitrogen oxides 36 remain dissolved within the water sample 14 because an equilibrium condition exists between the dissolved gaseous nitrogen oxides and ultraviolet-generated radical species which exist within the sample 14. To effectively remove the gaseous nitrogen oxides 36 from the water sample 14 for detection purposes, at least one carrier gas 40 is passed through the water sample 14 from a supply 42 schematically illustrated in FIG. 1. In this manner, the water sample 14 is effectively sparged by the carrier gas 40. The supply 42 may be compressed so that the carrier gas 40 is delivered under pressure to the water sample 14 through a tubular conduit member 43 having a first end 45 operatively connected to the supply 42 and a second end 46 immersed within the water sample 14. The second end 46 may optionally include a plurality of openings or perforations 47 therethrough (FIG. 1) in order to assist dispersion of the carrier gas 40 within the water sample 14. In an alternative embodiment (FIG. 2), the supply 42 of carrier gas 40 may be delivered to the water sample 14 using a pump 48 of conventional design (e.g. a standard centrifugal or diaphragm-type pump known in the art) which is positioned in-line within the conduit member 43.

The carrier gas 40 is delivered to (e.g. passed through) the water sample 14 during or immediately after the illumination process, and is passed therethrough at a preferred flow rate of about 25–1000 cc/min. (about 100–300 cc/min.= optimum). From a physical standpoint, the carrier gas 40 removes gaseous nitrogen oxides 36 within the water sample 14 by allowing fractional partitioning of the dissolved gaseous nitrogen oxides 36 across the water/carrier gas interface within the sample 14. In a preferred embodiment, the carrier gas 40 is selected from the group consisting of air, $N_2$, $O_2$, Ar, and other inert gases. Many different gases may be used as the carrier gas 40, provided that they are substantially inert relative to the water sample 14 and materials therein. If air is desired as the carrier gas 40, it is preferable that nitrogen oxide-free air be used. Nitrogen oxide-free air may be obtained by passing untreated air through commercially available filter units which are known in the art. However, normal (untreated) air may be used in connection with a predetermined calibration curve which takes into account ambient levels of gaseous nitrogen oxides in the untreated air. In this manner, ambient levels of gaseous nitrogen oxides can be considered when quantitative/ qualitative analyses are made.

Passing of the carrier gas 40 through the water sample 14 generates a gaseous stream 50 (FIGS. 1–2) which passes out of the water sample 14. The gaseous stream 50 consists of the carrier gas 40 in combination with any gaseous nitrogen oxides generated during ultraviolet illumination of the water sample 14. To analyze and detect gaseous nitrogen oxides within the gaseous stream 50, detector means 54 is provided. The detector means 54 is designed to qualitatively and/or quantitatively detect gaseous nitrogen oxides within the stream 50 in an accurate and rapid manner. Many different detection systems may be used as the detector means 54, and the present invention shall not be limited to any particular system. Two effective and preferred detection systems will consist of (1) a chemiluminescence nitrogen oxide detector; and (2) an electrochemical detector cell, both of which are well known in the art. Chemiluminescence detectors measure $NO_{(g)}$ concentration by detecting the luminescence emission produced when $NO_{(g)}$ and ozone are reacted. With respect to $NO_{2(g)}$, the chemiluminescence detector unit will, through an internal subsystem, catalytically reduce $NO_{2(g)}$ to $NO_{(g)}$ prior to analysis. An exemplary chemiluminescence detector suitable for use as the detector means 54 is commercially available from Monitor Labs, Inc. of Englewood, Colo. (USA) under the designation "Model 8840". If a chemiluminescence nitrogen oxide detector is used, it may be appropriate to pass the gaseous stream 50 through at least one ozone filter (not shown) prior to entry into the chemiluminescence detector so that any extraneous ozone is removed from the stream 50. The presence of ozone in the gaseous stream 50 can be undesirable in situations involving chemiluminescence detectors since ozone can create an interference condition which may yield inaccurate and biased data signals. An exemplary ozone filter suitable for use herein will consist of conventional filter paper treated with $NaNO_2$. However, the use of an ozone filter is not absolutely required, with the need for such a filter being determined by preliminary pilot studies.

An electrochemical detector system basically involves an amperometric gas sensor which detects $NO_{2(g)}$ via a reduction-oxidation reaction in a porous working electrode, and subsequently converts the electrode current to an output voltage representative of $NO_{2(g)}$ concentration. An exemplary electrochemical detector cell suitable for use as the detector means 54 is commercially available from Transducers Research, Inc. of Naperville, Ill. (USA) under the designation "Odyssey 2001™", and from Enmet Corporation of Ann Arbor, Mich. (USA) under the designation "Toximet™". It should be noted that both of the foregoing systems (electrochemical detector cells and chemiluminescence detectors) have specific advantages. While chemiluminescence detector units are capable of directly detecting $NO_{(g)}$ and indirectly detecting $NO_{2(g)}$ via internal catalytic reduction so that a total nitrogen oxide value can be obtained, they are generally large in size with minimal portability. In contrast, while many electrochemical cell systems are small and portable, most commercially available systems are only capable of detecting a single gas (e.g. $NO_{2(g)}$ or $NO_{(g)}$) and cannot provide data involving the total amount of nitrogen oxides in a mixture containing both $NO_{2(g)}$ and $NO_{(g)}$. However, electrochemical cells designed to detect $NO_{2(g)}$ may be used in this embodiment of the invention for numerous reasons, especially regarding the detection of nitrogen-containing ions as described above. First, the photolytic decomposition of nitrate ions in solution will result in the substantially exclusive production of $NO_{2(g)}$ as shown in reaction (1) above. Second, while the photolytic reduction of nitrite ions in solution will generate both $NO_{2(g)}$ and $NO_{(g)}$, most nitrite ions in solution are immediately oxidized to nitrate ions which produce $NO_{2(g)}$ upon illumination with ultraviolet light. As far as dissolved non-ionic nitro-containing compounds are concerned, they will generate $NO_{2(g)}$ during photolytic decomposition, possibly in combination with $NO_{(g)}$ depending on the type of composition under consideration. Since $NO_{2(g)}$ will, in fact, be generated during the application of ultraviolet light as described above, it can therefore be detected using an electrochemical cell system.

Other conventional systems suitable for use as the detector means 54 include but are not limited to ion mobility spectrometers, conventional calorimetric indicators, standard metalo-phathocynine detectors, as well as other systems known in art for gaseous nitrogen oxide detection.

To effectively analyze the gaseous stream 50 for gaseous nitrogen oxides, the detector means 54 is supplied with the stream 50 as soon as it leaves the water sample 14. As illustrated in FIGS. 1–2, the detector means 54 preferably includes a tubular conduit member 60 having a first end 62 connected to the detector means 54, and a second end 64 positioned directly adjacent the water sample 14 within the path of the gaseous stream 50. Using these components, the gaseous stream 50 will enter the second end 64 of the conduit member 60 as it exits the water sample 14. In a preferred embodiment, the second end 64 of the conduit member 60 should be positioned at a distance of about 0.5–5.0 cm (about 1–2 cm=optimum) from the water sample 14.

To facilitate entry of the gaseous stream 50 into the conduit member 60 and detector means 54, the second end 64 of the conduit member 60 may optionally consist of a cone or funnel-shaped collecting portion 68 as schematically illustrated in FIG. 1. However, the present invention shall not be limited to any particular configuration regarding the second end 64 of the conduit member 60.

Figure 3:
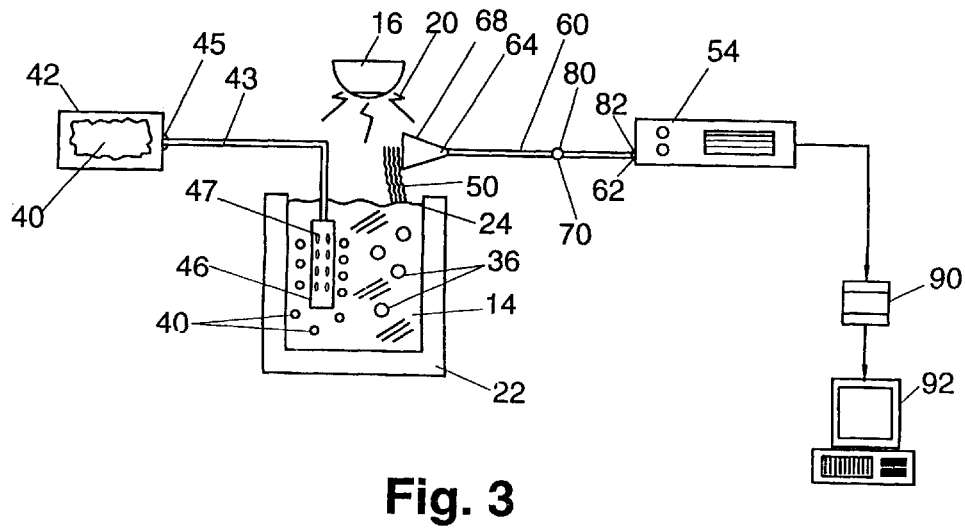
FIG. 3 is a schematic representation of a further modification to the process of FIG. 1 which involves the use of suction means to deliver gaseous reaction products to the detector means.

In an alternative embodiment schematically shown in FIG. 3, the gaseous stream 50 is supplied to the detector means 54 using suction means 70 for generating a negative pressure (e.g. a vacuum). The suction means 70 is in fluid communication with the detector means 54 (e.g. directly connected to or integrally positioned within the detector means 54) so that the gaseous stream 50 is drawn into the detector means 54. The suction means 70 may involve many different structural components, including but not limited to the apparatus illustrated in FIG. 3 which involves a vacuum pump system for drawing the gaseous stream 50 into the detector means 54. Specifically, a conventional vacuum pump 80 is positioned in-line between the first and second ends 62, 64 of the conduit member 60. Alternatively, the pump 80 may be positioned at the first end 62 of the conduit member 60, at the second end 64 thereof, or within the detector means 54. Any type of conventional pump system may be used as the pump 80 as long as it is capable of generating a negative pressure (e.g. suction), including but not limited to a diaphragm pump known in the art. In a preferred embodiment, the vacuum pump 80 will pump the gaseous stream 50 into the detector means 54 at a rate of about 50–500 cc/min. (about 100–200 cc/min=optimum). For the purposes of this invention, the detector means 54 and the suction means 70 shall collectively constitute a combined detection system 82 as illustrated in FIG. 3.

To operate the suction means 70, the second end 64 of the conduit member 60 (e.g. the funnel-shaped collecting portion 68) is positioned directly adjacent the water sample 14 within the path of the gaseous stream 50 in order to collect the stream 50. The preferred distance range between the second end 64 of the conduit member 60 and the water sample 14 in the embodiment of FIG. 3 is substantially the same as the corresponding range associated with the embodiment of FIGS. 1–2. The vacuum pump 80 functioning as suction means 70 is then activated in order to draw the gaseous stream 50 through the conduit member 60 and into the detector means 54. The detector means 54 is thereafter activated to provide a qualitative and/or quantitative analysis of gaseous nitrogen oxides within the stream 50.

In accordance with the foregoing processes, the positive detection of gaseous nitrogen oxides in the gaseous stream 50 provides a qualitative indication that dissolved nitro-containing compositions (especially nitrate and/or nitrite ions) were present in the water sample 14. The information is important and useful for a variety of purposes. As far as quantitative analyses are concerned, the amount of nitrate ions, nitrite ions, and/or dissolved non-ionic nitro-containing compounds in the water sample 14 may be derived in accordance with reference (control) samples containing such materials in specified amounts. From these control samples, a standardized data curve can be generated in accordance with conventional analytical techniques. This curve may then be used during actual testing procedures to obtain accurate quantitative information. If the test samples of interest are known to contain specific minerals and other materials which might influence gaseous nitrogen oxide production, any reference samples used to generate a standardized curve may be prepared with comparable materials added thereto so that accurate data can be obtained.

Data received from the detector means 54 may be correlated and converted into a usable format by operative connection of the detector means 54 to a data acquisition system 90 known in the art which is schematically illustrated in FIGS. 1–3. While the present invention shall not be limited to any particular data acquisition system, an exemplary system suitable for use as system 90 is commercially available from Biopac Systems, Inc. of Goleta, Calif. (USA) under the designation "MP-100". The data acquisition system 90 is thereafter connected to a standard computer unit 92. The computer unit 92 may involve many different systems, including but not limited to portable computers manufactured by the Apple Computer Co. of Cupertino, Calif. (USA) under the "Powerbook®" trademark.

Using the foregoing techniques, it is possible to detect very small quantities of dissolved nitro-containing compositions within the selected water sample. For example, nitrate/nitrite ion levels in water samples may be detected in amounts as low as about 0.1 mg of nitrate nitrogen/liter of water and about 0.1 mg of nitrite nitrogen/liter of water. Even lower detection limits may be possible through the selection of appropriate detector means and other system components as determined by preliminary studies.

B. Detection of Nitrate and/or Nitrite Compounds on Solid Materials

A second embodiment of the invention involves the detection of nitro-containing compositions (e.g. nitrate and/or nitrite compounds) on solid materials (substrates). This embodiment is especially useful in the detection of solid nitro-containing compositions ranging from fertilizers to nitrate/nitrite explosive materials and other compounds classified within the definition of "nitro-containing compositions" listed above. The terms "solid material", "solid substrate" and "solid composition" as used herein shall not be limited to any particular solid materials. Exemplary solid substrates appropriate for nitro-composition testing include soil samples, commercial packaging materials, shipping crates, containers of various form, and the like. Regarding packaging materials, containers, and shipping crates, the analysis of nitro-containing compositions from a qualitative perspective is especially important in the detection of nitrate and/or nitrite-based explosives. Examples of such explosives are listed above. As previously noted, an increasing demand has developed for technology involving the detection of explosive compositions in airports and other public areas vulnerable to terrorist activities.

Figure 4:
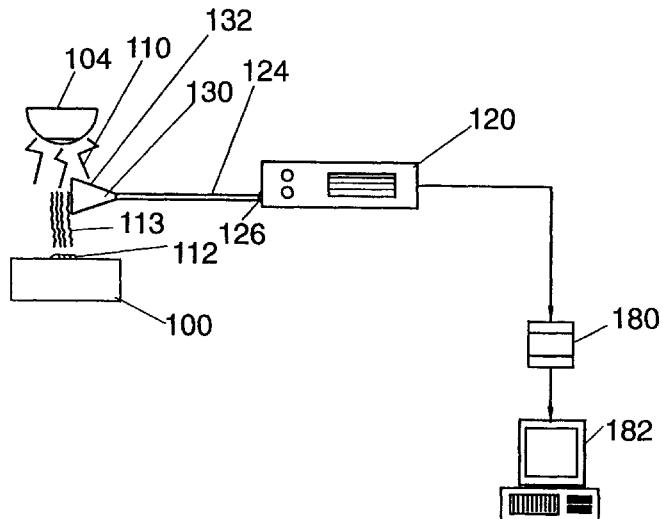
FIG. 4 is a schematic representation of an exemplary process used in connection with a second embodiment of the present invention to detect nitro-containing compositions (e.g. nitrate and/or nitrate compositions) on solid materials.

With reference to FIG. 4, a preferred method for detecting nitro-containing compositions (e.g. nitrate and/or nitrite compounds) on solid materials is schematically illustrated. A sample or portion of solid material 100 is initially provided which can involve many different compositions. The solid material 100 may be constructed of various packaging compositions (e.g. paper, wood, cardboard and cloth), as well as leather, plastic, glass, metal, human skin, and the like. Of particular interest regarding the detection of nitrate/nitrite explosives are materials used to manufacture luggage, suitcases, shipping crates, packing cartons, and the like.

Next, an ultraviolet light source 104 is provided. The light source 104 may involve many different illumination systems, and the present invention shall not be restricted to any single system. In this embodiment of the invention, portability of the light source 104 is an important consideration. The light source 104 should be capable of generating continuous or pulsed ultraviolet light having a continuous spectral wavelength output (e.g. spectral wavelength range distribution) of at least about 220–550 nm at a power output level of about 0.5–500 W (about 5–50 W=optimum). However, ultraviolet light sources having an even broader spectral output range may also be used as long as the foregoing preferred range is encompassed therein. The precise parameters to be selected in connection with the light source 104 will depend on a variety of factors including the type of light source 104 being used and the environment in which testing takes place. Specific wavelengths and power output levels for any given situation may ultimately be determined in accordance with preliminary pilot studies.

As noted above, the light source 104 (and most ultraviolet light sources) will not generate a single ultraviolet wavelength, but will instead generate ultraviolet light in the form of a continuum encompassing a broad wavelength range which includes the range of interest described above (e.g. at least about 220–550 nm). A preferred system for use as the light source 104 involves a battery powered ultraviolet flash lamp operating at a pulse frequency of about 1–22 Hz. This type of system is portable and appropriate for use at airports and other public facilities. An exemplary commercial flash lamp suitable for the purposes set forth herein will consist of a 24 V xenon flash lamp system sold by EG&G Electro-Optics, Inc of Salem, Mass. (USA) under the designation "MVS-2602/FX-249UV". Another system which may be used involves a standard 1000 W mercury vapor lamp capable of producing a continuous light output. However, flash lamp units are preferred in view of their low cost, portability, and high efficiency. Various additional ultraviolet light sources which may be used as the light source 104 are commercially available from Spectral Energy Corp. of Westwood, N.J. (USA).

The application of ultraviolet light 110 from the light source 104 causes the photolytic dissociation of nitro-containing compositions 112 on the solid material 100 in order to produce gaseous nitrogen oxides 113 therefrom (FIG. 1). The term "gaseous nitrogen oxides" shall be defined to encompass $NO_{2(g)}$ and/or $NO_{(g)}$ as noted above. In a preferred embodiment, the ultraviolet light source 104 will be positioned at a distance of about 1–20 cm (about 2–10 cm=optimum) from the solid material 100, with the ultraviolet light 110 being applied for a duration of about 15–300 seconds (about 30–120 seconds=optimum). As previously stated, these and other numerical parameters are provided for example purposes. Exact reaction conditions and parameters may vary in accordance with the equipment being used and the character of the compositions for which testing is desired.

To analyze and detect any gaseous nitrogen oxides which may be generated during ultraviolet illumination of the solid material 100, detector means 120 is provided. The detector means 120 is designed to qualitatively and/or quantitatively detect gaseous nitrogen oxides generated from any nitro-containing compositions (e.g. nitrate/nitrite compounds) on the solid material 100. Many different detection systems may be used as the detector means 120. In a preferred embodiment, the same detecting systems associated with detector means 54 can be used in connection with detector means 120. Two effective detection systems suitable for use as the detector means 120 will again consist of (1) a chemiluminescence nitrogen oxide detector; (2) and an electrochemical detector cell. Both of these systems and commercially-available examples thereof are described above. Accordingly, all of the information disclosed regarding the detector means 54 is equally applicable regarding detector means 120.

As previously noted, both of the foregoing systems have various advantages. While chemiluminescence detector units are capable of directly detecting $NO_{(g)}$ and indirectly detecting $NO_{2(g)}$ via internal catalytic reduction so that a total gaseous nitrogen oxide value can be obtained, they are generally large and non-portable. In contrast, many electrochemical cell systems are highly portable and suitable for use in public places. However, most electrochemical cells are only capable of detecting a single gas (e.g. $NO_{2(g)}$ or $NO_{(g)}$), and cannot provide data involving the total amount of nitrogen oxides in a mixture containing both $NO_{2(g)}$ and $NO_{(g)}$. Notwithstanding these limitations, electrochemical cells designed to detect $NO_{2(g)}$ are suitable for use in this embodiment of the invention. Specifically, the photolysis of substantially all of the nitro-containing compositions in accordance with the foregoing definition (including nitrate/nitrite compounds) will generate $NO_{2(g)}$, thereby allowing qualitative detection of such materials using electrochemical cell technology. Qualitative detection is of primary concern in this embodiment of the invention, especially in the analysis of solid materials for explosives.

Regarding quantitative analysis, electrochemical cells may be used by initially generating calibration curves involving $NO_{2(g)}$ production when standard reference samples are illuminated with ultraviolet light. These calibration curves may then be used to correlate $NO_{2(g)}$ production with the amount of nitro-containing compositions (e.g. nitrate/nitrite materials) actually present on the solid material 100. It should also be noted that other systems may be used as the detector means 120, including ion mobility spectrometers, conventional calorimetric indicators, and standard metalo-phathocynine detectors.

To effectively analyze and detect any gaseous nitrogen oxides generated during ultraviolet illumination of the solid material 100, the detector means 120 must be supplied with any gaseous nitrogen oxides as soon as they are generated, and thereafter activated to accomplish nitrogen oxide detection. To accomplish this, the detector means 120 (or any sampling components attached to and part of the detector means 120) is positioned directly adjacent the solid material 100 during ultraviolet illumination so that the gaseous nitrogen oxides 113 can enter into the detector means 120 as illustrated in FIG. 4. In a preferred embodiment, the detector means 120 will include a tubular conduit member 124 having a first end 126 connected to the detector means 120, and a second end 130 positioned directly adjacent the sample of solid material 100 and within the path of any generated gaseous nitrogen oxides. As a result, the gaseous nitrogen oxides 113 will enter the second end 130 of the conduit member 124 during ultraviolet illumination of the solid material 100. In a preferred embodiment, the second end 130 of the conduit member 124 will be positioned at a distance of about 0.5–5.0 cm (about 1.0–2.0 cm=optimum) from the solid material 100.

To facilitate entry of the gaseous nitrogen oxides into the conduit member 124 and detector means 120, the second end 130 of the conduit member 124 may optionally consist of a cone or funnel-shaped collecting portion 132 illustrated in FIG. 4. However, the present invention shall not be limited to any particular configuration regarding the second end 130 of the conduit member 124.

Figure 5:
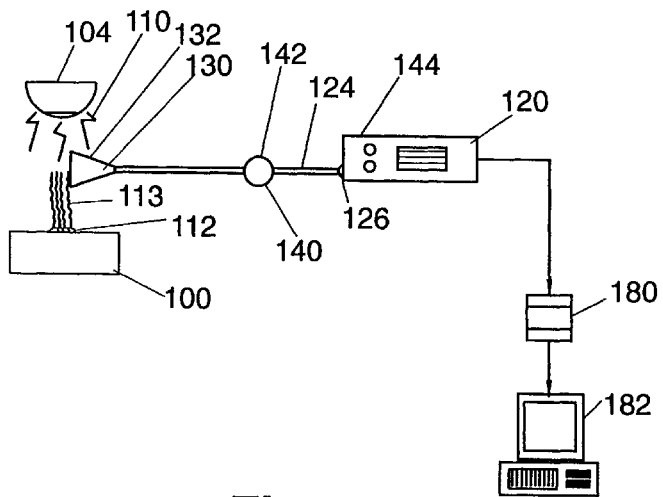
FIG. 5 is a schematic representation of a modification to the process of FIG. 4 which involves the use of suction means to deliver gaseous reaction products to the detector means.

In an alternative embodiment schematically shown in FIG. 5, any gaseous nitrogen oxides may be supplied to the detector means 120 using suction means 140 for generating a negative pressure (e.g. a vacuum). The suction means 140 is in fluid communication with the detector means 120 (e.g. directly connected to or integrally positioned within the detector means 120) so that any gaseous nitrogen oxides are drawn into the detector means 120. The suction means 140 may involve many different structural components, including but not limited to the system illustrated in FIG. 5 which uses a vacuum pump. In the embodiment of FIG. 5, a conventional vacuum pump 142 is positioned in-line between the first and second ends 126, 130 of the conduit member 124. Alternatively, the pump 142 may be positioned at the first end 126 of the conduit member 124, at the second end 130 thereof, or within the detector means 120. Any standard pump capable of generating negative pressures may be used as pump 142, including a diaphragm pump of the same type described above regarding pump 80. In a preferred embodiment, the pump 142 will be operated so that any gaseous nitrogen oxides are drawn into the detector means 120 at a rate of about 50–1000 cc/min. (about 100–200 cc/min=optimum). For the purposes of this invention, the detector means 120 and suction means 140 shall collectively constitute a combined detection system 144 shown in FIG. 5.

To operate the suction means 140, the second end 130 of the conduit member 124 (e.g. the funnel-shaped collecting portion 132) is positioned directly adjacent the sample of solid material 100 within the path of any evolved gaseous nitrogen oxides. The preferred distance range between the second end 130 of the conduit member 124 and the solid material 100 in the embodiment of FIG. 5 is substantially the same as the range listed above in connection with the embodiment of FIG. 4. The pump 142 (e.g. suction means 140) is then activated in order to draw any gaseous nitrogen oxides (e.g. element 113 in FIG. 5) through the conduit member 124 and into the detector means 120. Thereafter, the detector means 120 is activated to provide a qualitative and/or quantitative analysis of any gaseous nitrogen oxides generated during the illumination process.

Figure 6:
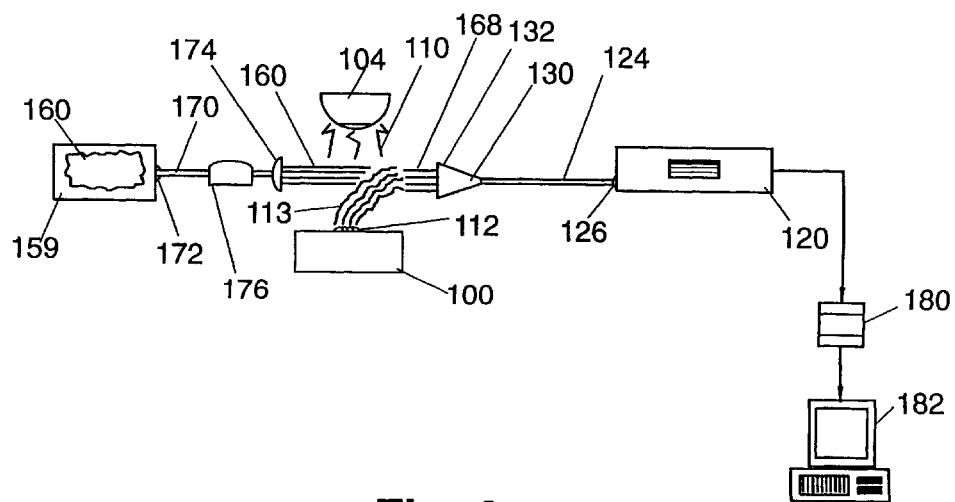
FIG. 6 is a schematic representation of a further modification to the process of FIG. 4 which involves the use of a carrier gas to facilitate the delivery of gaseous reaction products to the detector means.

A further modification of the system shown in FIG. 4 is schematically illustrated in FIG. 6. The system of FIG. 6 includes a supply 159 of a carrier gas 160 which is passed directly over and in contact with the solid material 100 during ultraviolet illumination. As a result, the carrier gas 160 combines with any gaseous nitrogen oxides (reference number 113 in FIG. 6) generated during illumination of the solid material 100. The carrier gas 160 (and any gaseous nitrogen oxides combined therewith) are then supplied to the detector means 120 for analysis in the form of a gaseous stream 168. The gaseous stream 168 will include the carrier gas 160 in combination with any gaseous nitrogen oxides generated during the foregoing process. The use of carrier gas 160 in this manner isolates photolytically-generated nitrogen oxides from the surrounding environment during delivery to the detector means 120. This procedure is especially useful in environments containing large ambient quantities of nitrogen oxides (e.g. airports and the like).

The supply 159 of carrier gas 160 may be compressed so that the gas 160 is delivered under pressure to the solid material 100. In the embodiment of FIG. 6, delivery is accomplished through a tubular conduit member 170 having a first end 172 operatively connected to the supply 159 and a second end 174 positioned adjacent the solid material 100 (e.g. at a preferred distance of about 0.5–5.0 cm therefrom [about 1.0–2.0 cm=optimum]). Alternatively as shown in FIG. 6, the carrier gas 160 may be delivered to the solid material 100 using a pump 176 of conventional design (e.g. a standard centrifugal or diaphragm pump) which is positioned in-line within conduit member 170. The carrier gas 160 is delivered to the solid material 100 at a preferred flow rate of about 50–1000 cc/min. (about 100–200 cc/min.= optimum). In this manner, the carrier gas 160 effectively combines with the gaseous nitrogen oxides 113 shown in FIG. 6 to produce the gaseous stream 168.

In a preferred embodiment, the carrier gas 160 is selected from the group consisting of air, $N_2$, $O_2$, Ar, and other inert gases. Accordingly, many different carrier gases may be used as the gas 160, provided that they are substantially inert relative to the solid material 100 and any nitro-containing compositions (e.g. nitrate/nitrite materials) thereon. If air is desired as the carrier gas 160, it is preferable that nitrogen oxide-free air be used. Nitrogen oxide-free air may be obtained in the same manner described above regarding the embodiment of FIGS. 1–3. However, normal (untreated) air may be used in connection with calibration curves which consider ambient nitrogen oxide levels in the untreated air.

Figure 7:
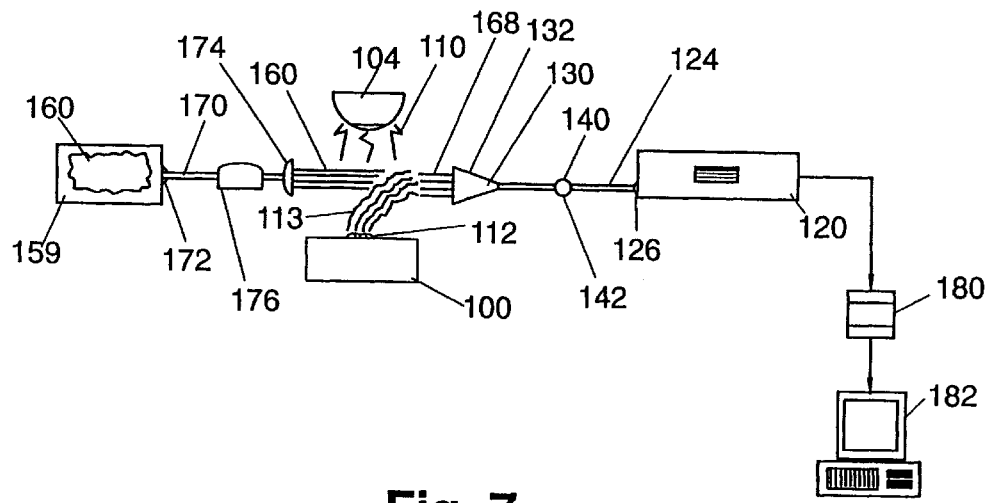
FIG. 7 is a schematic representation of a modification to the process of FIG. 6 which involves the use of suction means to deliver the gaseous stream produced by the carrier gas to the detector means.

Numerous methods exist for supplying the detector means 120 with the gaseous stream 168 during ultraviolet illumination of the solid material 100. For example, the second end 130 of the conduit member 124 associated with the detector means 120 can be placed adjacent to or in direct contact with (e.g. in the path of) the gaseous stream 168 as it leaves the solid material 100 (FIG. 6). This approach can be used regardless of whether the second end 130 of the conduit member 124 includes the funnel-shaped collecting portion 132. In the embodiment of FIG. 7, suction means 140 for generating a negative pressure (e.g. pump 142) can be used in the same manner described above in the embodiment of FIG. 5 to draw the gaseous stream 168 into the detector means 120. To operate the suction means 140, the second end 130 of the conduit member 124 is positioned directly in the path of the gaseous stream 168 as it leaves the solid material 100. The pump 142 (e.g. suction means 140) is then activated in order to draw the gaseous stream 168 through the conduit member 124 and into the detector means 120.

Upon the application of ultraviolet light 110 to the solid material 100, the detector means 120 is activated to determine if any gaseous nitrogen oxides (especially $NO_{2(g)}$) were photolytically generated. If gaseous nitrogen oxides are positively detected, it can be concluded that the solid material 100 contained at least one nitro-containing composition (e.g. nitrate and/or nitrite compound) thereon. Detection in this manner is of considerable importance, especially when explosive compositions are involved. As far as nitrate-type explosives and other nitrate materials are concerned, use of the foregoing method enables the detection of such compositions on solid substrates in amounts as low as about 1.0 µg, and nitrite-type explosives as well as other nitrite materials in amounts as low as about 1.0 µg. Even lower detection limits may be possible through the selection of appropriate detector means and other system components as determined by preliminary tests.

As far as quantitative analyses are concerned, a determination of the total amount of nitro-containing compositions (e.g. nitrate and/or nitrite materials) on a solid substrate may be undertaken in accordance with reference (control) samples involving specified amounts of such compositions. Irradiation of control samples to generate gaseous nitrogen oxides enables a standardized data curve to be produced using conventional techniques. This curve may then be used during actual testing procedures to obtain accurate quantitative information. Data received from the detector means 120 may be correlated and converted into a usable format by operative connection of the detector means 120 to a data acquisition system 180 known in the art which is schematically illustrated in FIGS. 4–7. While the present invention shall not be limited to any particular data acquisition system, an exemplary system suitable for use as system 180 is commercially available from Biopac Systems, Inc. of Goleta, Calif. (USA) under the designation "MP-100". The data acquisition system 180 is thereafter connected to a standard computer unit 182. The computer unit 182 may likewise involve many different commercially available products including but not limited to portable computer systems manufactured by the Apple Computer Co. of Cupertino, Calif. (USA) under the "Powerbook®" trademark.

Figure 8:
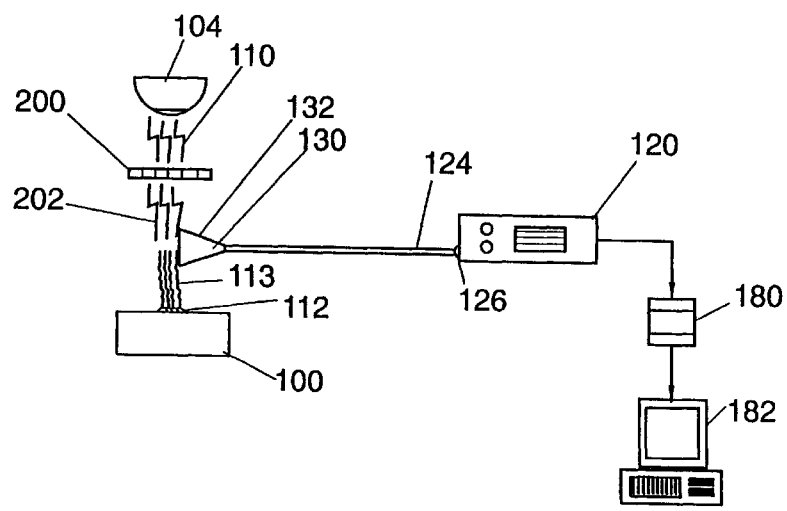
FIG. 8 is a schematic representation of a still further modification to the process of FIG. 4 which involves the application of ultraviolet light to a sample of solid material at a selected wavelength using a wavelength control system in order to detect a specific nitro-containing composition of interest.

A still further modification of the system of FIG. 4 is illustrated in FIG. 8. Specifically, the system of FIG. 8 is substantially identical to the system of FIG. 4 except as indicated below. In certain cases, it may be desirable to use the system of FIG. 4 to determine if a specific nitro-containing composition is present on the selected solid substrate by using ultraviolet light having a specific wavelength known to dissociate the composition of interest. This procedure is especially useful in connection with nitrate/nitrite explosive materials. For example, if the detection a specific explosive is desired, ultraviolet light having a wavelength known to dissociate the explosive is applied to the sample of solid material. Thereafter, the steps described above in connection with the system of FIG. 4 can be undertaken (including the use of detector means) to determine if any gaseous nitrogen oxides are generated. If gaseous nitrogen oxides are present, it can be concluded that the solid material had the explosive composition of interest thereon. It should be noted that this embodiment of the invention shall not be exclusively limited to the detection of nitrate/nitrite explosive materials, and is applicable to other nitro-containing compositions (e.g. nitrate/nitrite fertilizers) encompassed within the definition of "nitro-containing compositions" set forth above. Furthermore, depending on the specific detector means being used, further information may be obtained including quantitative data regarding the amount of generated gaseous nitrogen oxides. This quantitative information may be correlated with standardized data curves to provide accurate information regarding the amount of designated nitro-containing composition on the solid material.

With specific reference to FIG. 8, the system of FIG. 4 is illustrated which has been modified for the purposes described above. In order to implement the process of FIG. 8, a nitro-containing composition which photolytically dissociates at a known ultraviolet wavelength (or wavelength range) is first selected/chosen for detection purposes. For example, the selected composition could involve one of many nitrate/nitrite explosives which may be encountered in airports or other public facilities. Selected commercially available explosive compositions and their dissociation/activation ultraviolet wavelengths are listed below in TABLE I:

TABLE I

| COMPOUND | WAVELENGTH (nm) |
|---|---|
| Ammonium nitrate | 260–275 |
| RDX | 330–335 |
| PETN | 260–275 |
| HMX | 500–505 |

Further information regarding the foregoing explosive compositions is listed above. With reference to FIG. 8, the same type of ultraviolet light source 104 is used as described above relative to FIG. 4. As previously noted, the light source 104 normally generates ultraviolet light in the form of a continuum encompassing a broad wavelength range. However, the system of FIG. 8 includes a wavelength control system 200 positioned in front of or integrally located within the ultraviolet light source 104 so that ultraviolet light from the source 104 will pass into and through the wavelength control system 200. The wavelength control system 200 is designed to produce an ultraviolet light fraction 202 (FIG. 8) from the ultraviolet light 110 having desired wavelength characteristics (e.g. a desired wavelength or wavelength range). Many different systems may be used as the wavelength control system 200, and the present invention shall not be limited to the use of any particular components or devices in this regard. For example, the wavelength control system 200 may consist of a grating monochromator which is generally known in the art for ultraviolet wavelength selection. Exemplary monochromator systems suitable for use herein are commercially available from numerous sources including but not limited to Spectral Energy Corp. of Westwood, N.J. (USA)—(model nos. GM 252, GM 100, and GM 200). The specific commercial monochromator unit to be selected for any given application will depend on the ultraviolet wavelength of interest and other factors. Monochromators generally operate by collecting incoming light using a collimating mirror and supplying the light to a diffraction grating. The diffraction grating thereafter separates the light into its desired components. Other devices suitable for use as the wavelength control system 200 involve bandpass filter units/systems which are known in the art for ultraviolet wavelength control. Specifically, one or more wavelength interference filters are used to selectively allow the transmission of light with a desired wavelength while blocking the passage of light having different wavelength characteristics. An exemplary commercial wavelength filter system is available from Spectral Energy Corp. of Westwood, N.J. (USA)—(model no. FM-1).

Illumination of the solid material 100 with the ultraviolet light fraction 202 having the desired wavelength characteristics as illustrated in FIG. 8 will enable detection of the nitro-containing composition of interest (which dissociates at the selected wavelength or wavelength range.)

Specifically, the detector means 120 is positioned adjacent the sample of solid material 100 so that any generated gaseous nitrogen oxides will enter the detector means 120. Thereafter, the detector means 120 is activated as described above in order to determine whether any gaseous nitrogen oxides were generated during the illumination process. The generation of any gaseous nitrogen oxides 113 and detection thereof using the detector means 120 as illustrated in FIG. 8 will provide a positive indication that the desired nitro-containing composition (e.g. nitrate/nitrite explosive) was present on the sample of solid material 100. Again, this variation of the embodiment of FIG. 4 shall not be limited to the detection of any particular nitro-containing compositions and the use of any specific ultraviolet light wavelengths. It is also contemplated that the embodiment of FIG. 8 may be modified as desired to include the use of suction means 140 (FIG. 5), a carrier gas 160 (FIG. 6) or both (FIG. 7). Finally, implementation of the embodiment of FIG. 8 in the most effective manner may involve the use of preliminary pilot studies on the compositions of interest to determine the proper ultraviolet wavelengths and other operational parameters.

Figure 9:
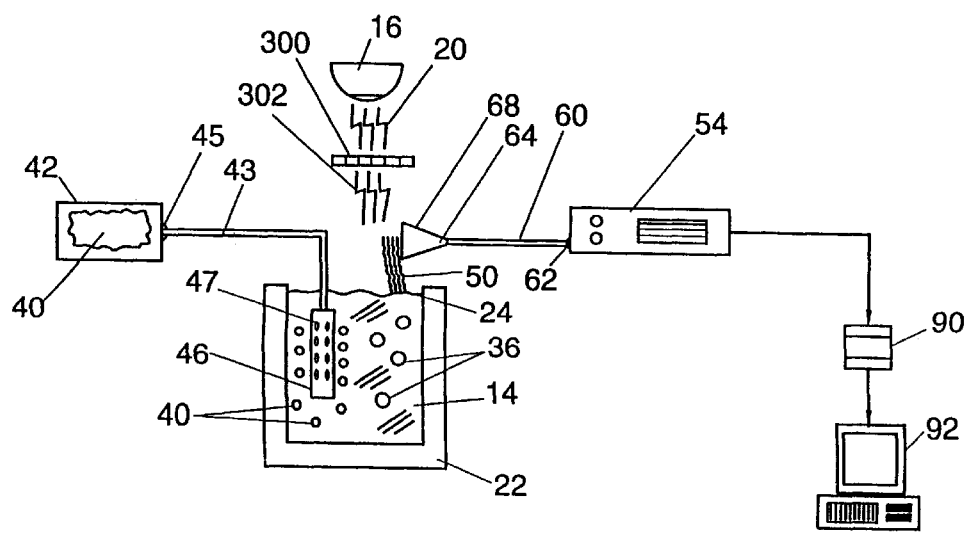
FIG. 9 is a schematic representation of a modification of the processes of FIGS. 1 and 8 which involves the application of ultraviolet light to a water sample at a selected wavelength using a wavelength control system in order to detect a specific dissolved nitro-containing composition of interest.

The foregoing techniques used to detect specific nitro-containing compositions shall also be applicable to the detection of specific dissolved nitro-containing compositions (e.g. dissolved explosives and other compositions) in water samples. A system suitable for this purpose is illustrated in FIG. 9 which involves a modification of the system shown in FIG. 1. Furthermore, all of the information described above relative to the embodiment of FIG. 8 shall be equally applicable to the embodiment of FIG. 9 unless otherwise noted. With reference to FIG. 9, a specific dissolved nitrogen-containing composition for which testing is desired is first selected. The same type of ultraviolet light source 16 associated with FIG. 1 is used in the testing procedure. As previously noted, the light source 16 normally generates ultraviolet light in the form of a continuum encompassing a broad wavelength range. However, the system of FIG. 9 further includes a wavelength control system 300 positioned in front of or integrally located within the ultraviolet light source 16 so that ultraviolet light from the activated source 16 can pass into and through the wavelength control system 300. The wavelength control system 300 is designed to produce an ultraviolet light fraction 302 having desired wavelength characteristics (e.g. a desired wavelength or wavelength range) suitable for dissociating the dissolved nitro-containing composition of interest. Many different systems may be used as the wavelength control system 300, and the present invention shall not be limited to any particular systems and components for this purpose. For example, the wavelength control system 300 may involve the same types of devices described above regarding wavelength control system 200 (e.g. a grating monochromator and/or bandpass filter units/systems which are known in the art for ultraviolet wavelength control).

Illumination of the water sample 14 with the ultraviolet light fraction 302 having the selected wavelength (or wavelength range) will enable detection of the dissolved nitro-containing composition of interest (e.g. dissolved non-ionic explosive compositions such as TNT) which dissociates at the selected wavelength. This is accomplished by passing the carrier gas 40 through the water sample 14 during or immediately after illumination thereof in order to generate the gaseous stream 50 which is thereafter supplied to the detector means 54. The detector means 54 is then activated as described above in order to determine if any gaseous nitrogen oxides are present in the gaseous stream 50. The generation of any gaseous nitrogen oxides and detection thereof using the detector means 54 as illustrated in FIG. 9 will provide a positive indication that the designated dissolved nitro-containing composition (e.g. nitrate/nitrite explosive) was present within the water sample 14. Again, this variation of the embodiment of FIG. 1 shall not be limited to the detection of any particular nitro-containing compositions and the use of any specific ultraviolet light wavelengths. It is also contemplated that the embodiment of FIG. 9 may be modified as desired to include the use of suction means 70 as illustrated in FIG. 3 and described above. Finally, implementation of the embodiment of FIG. 9 in the most effective manner may again involve the use of preliminary pilot studies on the compositions of interest to determine the proper ultraviolet wavelengths and other operational parameters.

The present invention represents a significant advance in analytical technology regarding the detection of nitro-containing compositions in various environments. The detection of such compositions is accomplished in a rapid and efficient manner without the need for elaborate testing systems and chemical reagents. These goals are achieved through the photolytic dissociation of such materials (e.g. nitrate/nitrite compounds) in order to generate gaseous nitrogen oxides which are thereafter detected as described above. This aspect of the invention in which gaseous nitrogen oxides are photolytically generated using ultraviolet light and thereafter detected represents a substantial departure from prior detection systems and provides numerous benefits.

Having herein described preferred embodiments of the present invention, it is anticipated that suitable modifications may be made thereto by individuals skilled in the art which nonetheless remain within the scope of the invention. In this regard, the present invention shall only be construed in accordance with the following claims:

The invention that is claimed is:

1. A method for analyzing a sample of solid material for the presence of nitro-containing compositions thereon, said method comprising the steps of:

providing an ultraviolet light source for generating ultraviolet light;

providing a sample of solid material comprising an uncovered and exposed surface, said uncovered and exposed surface allowing said ultraviolet light from said ultraviolet light source to be applied to said solid material without passing through any intervening structures;

positioning said ultraviolet light source directly above said uncovered and exposed surface of said solid material in order to create an uninterrupted gap between said solid material and said light source;

activating said ultraviolet light source so that said light source delivers said ultraviolet light into said gap and onto said uncovered and exposed surface of said solid material without interruption by any intervening structures, said ultraviolet light photolytically dissociating any of said nitro-containing compositions on said solid material into gaseous nitrogen oxides, said gaseous nitrogen oxides rising upwardly from said surface of said solid material;

providing gas detector means for detecting gaseous nitrogen oxides;

positioning at least a portion of said gas detector means above said uncovered and exposed surface of said solid material in order to create an uninterrupted gap between said solid material and said gas detector means so that any of said gaseous nitrogen oxides generated during delivery of said ultraviolet light onto said solid material will enter into said portion of said gas detector means without interruption by any intervening structures; and activating said gas detector means in order to determine if any of said gaseous nitrogen oxides were generated during delivery of said ultraviolet light onto said solid material.

2. A method for analyzing a sample of solid material for the presence of nitro-containing compositions thereon, said method comprising the steps of:

providing an ultraviolet light source for generating ultraviolet light;

providing a sample of solid material comprising an uncovered and exposed surface, said uncovered and exposed surface allowing said ultraviolet light from said ultraviolet light source to be applied to said solid material without passing through any intervening structures;

positioning said ultraviolet light source directly above said uncovered and exposed surface of said solid material in order to create an uninterrupted gap between said solid material and said light source;

activating said ultraviolet light source so that said light source delivers said ultraviolet light into said gap and onto said uncovered and exposed surface of said solid material without interruption by any intervening structures, said ultraviolet light photolytically dissociating any of said nitro-containing compositions on said solid material into gaseous nitrogen oxides, said gaseous nitrogen oxides rising upwardly from said surface of said solid material;

providing gas detector means for detecting gaseous nitrogen oxides;

passing a stream of at least one carrier gas over said surface of said solid material during delivery of said ultraviolet light onto said solid material, said carrier gas combining with any of said gaseous nitrogen oxides produced during delivery of said ultraviolet light in order to generate a gaseous stream which comprises said carrier gas in combination with said gaseous nitrogen oxides;

positioning at least a portion of said gas detector means above said uncovered and exposed surface of said solid material in order to create an uninterrupted gap between said solid material and said gas detector means so that said gaseous stream will enter into said portion of said gas detector means without interruption by any intervening structures; and activating said gas detector means in order to determine if any of said gaseous nitrogen oxides are present in said gaseous stream.

* * * * *